(12) United States Patent
Wylie et al.

(10) Patent No.: US 11,660,290 B2
(45) Date of Patent: *May 30, 2023

(54) AFFINITY BASED DRUG RELEASE FORMULATIONS

(71) Applicant: McMaster University, Hamilton (CA)

(72) Inventors: Ryan Wylie, Hamilton (CA); Vincent Huynh, Maple (CA)

(73) Assignee: McMaster University, Hamilton (CA)

( * ) Notice: Subject to any disclaimer, the term of this patent is extended or adjusted under 35 U.S.C. 154(b) by 427 days.

This patent is subject to a terminal disclaimer.

(21) Appl. No.: 16/780,226

(22) Filed: Feb. 3, 2020

(65) Prior Publication Data

US 2020/0171004 A1  Jun. 4, 2020

Related U.S. Application Data

(63) Continuation of application No. 15/615,429, filed on Jun. 6, 2017, now Pat. No. 10,576,061.

(60) Provisional application No. 62/345,958, filed on Jun. 6, 2016.

(51) Int. Cl.
| | | |
|---|---|---|
| *A61K 31/4188* | (2006.01) | |
| *A61K 38/00* | (2006.01) | |
| *A61K 47/69* | (2017.01) | |
| *A61K 31/4166* | (2006.01) | |
| *A61K 31/381* | (2006.01) | |
| *A61K 47/66* | (2017.01) | |

(52) U.S. Cl.
CPC ........ *A61K 31/4188* (2013.01); *A61K 31/381* (2013.01); *A61K 31/4166* (2013.01); *A61K 38/00* (2013.01); *A61K 47/665* (2017.08); *A61K 47/6903* (2017.08)

(58) Field of Classification Search
None
See application file for complete search history.

(56) References Cited

U.S. PATENT DOCUMENTS

| | | |
|---|---|---|
| 6,589,549 B2 | 7/2003 | Shih et al. |
| 6,723,344 B2 | 4/2004 | Sakiyama-Elbert et al. |
| 10,576,061 B2 * | 3/2020 | Wylie ............... A61K 47/6903 |
| 2007/0141105 A1 | 6/2007 | Stein et al. |
| 2008/0255004 A1 | 10/2008 | Neurauter et al. |
| 2011/0300127 A1 | 12/2011 | Nakamura et al. |
| 2012/0076773 A1 | 3/2012 | Sargeant |

OTHER PUBLICATIONS

Pakulska, M.M., et al., Affinity-Based Release of Chondroitinase ABC from a Modified Methylcellulose Hydrogel, J. of Controlled Release, 171(1): Oct. 10, 2013, 11-16.
Wieduwild, R., et al,. "A Repertoire of Peptide Tags for Controlled Drug Release from Injectable Noncovalent Hydrogel", Biomacromolecules, , 2014, 15(6):2058-2066.
Gao, Y., et al., "Thiolated Human Serum Albumin Cross-Linked Dextran Hydrogels as a Macroscale Delivery System", Soft Matter, 2014, 10(27): 4869-4874.
Vulic, K., et al., "Tunable Growth Factor Delivery from Injectable Hydrogels for Tissue Engineering", J. Am. Chem. Soc., 2012, 134(2): 882-885.
Lin, CC., et al., "Controlling Affinity Binding with Peptide-Functionalized Poly(ethylene glycol) Hydrogels", Adv. Func. Mater, 2009, 19(14): 2325.
Tae, G., et al., "PEG-Cross-Linked Heparin is an Affinity Hydrogel for Sustained Release of Vascular Endothelial Growth Factor" J. Biomater Sci. Polym. Ed., 2006, 17(1-2): 187-197.
Hirsch, "Easily reversible desthiobiotin binding to streptavidin, avidin, and other biotin-binding proteins: uses for protein labeling, detection, and isolation", Analytical Biochemistry, vol. 308, pp. 343-357, 2002.

* cited by examiner

*Primary Examiner* — Robert T. Crow
*Assistant Examiner* — John P Nguyen
(74) *Attorney, Agent, or Firm* — Bereskin & Parr LLP/S.E.N.C.R.L., s.r.l.; Sandra Marone

(57) ABSTRACT

The present application describes a two-step drug delivery formulation comprising a high affinity interaction between a drug conjugate and a compound, followed by introduction of a second compound with higher affinity to the drug conjugate to facilitate drug release. Delivery methods and specific interactions are also described.

18 Claims, 11 Drawing Sheets

A)

B)

C)

AFFINITY BASED DRUG RELEASE FORMULATIONS

RELATED APPLICATIONS

The present application is a continuation of co-pending U.S. patent application Ser. No. 15/615,429, filed Jun. 6, 2017, which claims the benefit of priority from U.S. provisional patent application No. 62/345,958 filed on Jun. 6, 2016, the contents of each of which are incorporated herein by reference in their entirety.

FIELD OF THE APPLICATION

The present application relates to affinity-based release formulations for drug delivery, for example formulations for the sustained release of a drug over time.

BACKGROUND OF THE APPLICATION

Retinal drug delivery remains a formidable challenge. Simple delivery methods results in poor drug distribution. Only 5% of topically applied drug enters the eye with <1% reaching the posterior segment.[1] The blood retinal barrier also limits intravenous drug delivery to the retina. Therefore, intravitreal, subconjunctival or subretinal injections are the most efficient delivery methods.[2] Current treatments for many retinal diseases involving pathological angiogenesis require the monthly intravitreal injection of a highly concentrated solution of Avastin® (bevacizumab), which may lead to systemic side effects.[3] There is a great need to develop systems that dramatically decrease injection frequency to increase patient compliance, lower health care costs, decrease ocular complications (e.g., acute onset endophtahlmitis, pseudo-endophthalmitis, cataract progression, retinal detachment and hemorrhage),[4,5] and minimize the risk of infections and systemic side effects,[6] which will in turn allow us to deliver a larger selection of drugs. Hydrogels are an ideal vehicle for intravitreal drug delivery since they are injectable, biocompatible and hold large drug payloads.[7] Even though hydrogels limit potential systemic side effects, their use clinically has been limited since they only marginally decrease injection frequency (every 2-3 months).[3,8,9]

Protein and antibody therapeutics are becoming an increasing prevalent class of drugs due to selectivity, potency, and limited side effects compared to small molecule drugs.[10] However, their short half-life and susceptibility to enzymatic degradation makes administration and delivery challenging. Often, invasive procedures are required to delivery proteins to specific locations. As such, drug loaded biomaterials have been proposed as protein delivery vehicles. Furthermore, many protein drugs require repeated and frequent doses due to their short half-life.

An emerging strategy for the sustained release of protein is through reversible affinity interactions. Affinity is often used to describe the favourable noncovalent interaction between two macromolecules, often involving electrostatic, Van der Waals, or hydrophobic interactions between two binding partners.[11] As many proteins have inherent affinities with extracellular matrix proteins (e.g., basic fibroblast growth factor), affinity controlled release through mimicking the extracellular matrix is an appealing strategy.[12] This method attenuates the initial burst release seen in many other delivery vehicles. The reversible affinity of many ligands can be exploited in order to create a system where release is dictated by the binding and unbinding kinetics as well as Fickian diffusion kinetics.[13]

SUMMARY OF THE APPLICATION

The present application describes formulations, kits, uses and methods based on a highly tunable two step physical interaction mechanism that eliminates passive drug diffusion and allows for highly controlled release of drugs. This unique drug delivery system may represent a major improvement, for example, for macromolecule delivery.

The biotin-streptavidin binding pair is a well-known affinity pair, often used in many biological assays. Their near covalent interaction ($K_d$ $10^{-15}$ M) has been utilized in numerous settings where chemical modification is not ideal.[14] This frequent usage has resulted in the production different analogues of streptavidin and biotin with differing affinities. Point mutations at the binding site of streptavidin have resulted in mutants such as captavidin (pH sensitive), traptavidin, and neutravidin, each with different binding altered binding affinities to biotin.[15,16,17] In addition to mutations to the protein of streptavidin, several different biotin derivatives with altered binding affinities have been developed, among these are iminobiotin and desthiobiotin,[14,18] further creating a diverse range of binding partners that can for use in varying applications. Therefore, in some embodiments the versatile streptavidin interactions are used to design affinity release formulations.

In some embodiments a two-step drug release mechanism involving reversible (e.g. streptavidin-desthiobiotin) and irreversible (e.g. streptavidin-biotin) physical interactions to gain unprecedented control over drug release rates is used. In an exemplary embodiment, therapeutics such as Avastin® (bevacizumab) are modified with streptavidin. Streptavidin-Avastin® (bevacizumab) is immobilized in desthiobiotin functionalized hydrogels, and is only released in the presence of biotin (see FIG. 1). Therefore, the streptavidin-Avastin® (bevacizumab) release may be controlled by controlling the soluble concentration of biotin in the hydrogel. While not wishing to be limited by theory, the drug release mechanism is explained by the competitive binding of desthiobiotin and biotin to streptavidin. Additionally, the hydrogels were modified by functionalization with streptavidin using strain promoted azide alkyne cycloaddition (SPAAC) and desthiobiotinylated Avastin® (bevacizumab) is prepared to create a reverse system where a minimally modified antibody is released (see FIG. 2).

Biotin's relatively high aqueous solubility results in the rapid release of streptavidin molecules. Therefore, hydrophobic biotins with lower solubility were synthesized. Only the soluble portion of the hydrophobic biotin will displace streptavidin from the hydrogel polymer backbone, releasing the streptavidin-drug conjugate. By tuning the solubility of the biotin, a controlled rate of displacement may be achieved. In the reverse system (e.g. FIG. 2), a similar concept is utilized, resulting in the delivery of a minimally modified drug conjugate. This reverse system is thus amenable to the sustained long term delivery of various therapeutics due to minimal modification resulting in a decrease possibility of a loss in drug efficacy.

This two step affinity controlled drug delivery system and formulation may be incorporated into either injectable or implantable hydrogels. Hydrogels due to their high water content and biocompatibility make them the most suitable drug delivery vehicles to house the drug delivery systems of the present application, allowing for long term sustained release of a desired therapeutic.

Accordingly the present application includes a drug release formulation comprising:
  (a) a drug conjugate comprising a drug bound to a first member of an affinity binding pair;
  (b) a second member of the affinity binding pair, wherein the drug conjugate reversibly binds to the second member of the affinity binding pair to form a complex; and
  (c) a competitive binding compound that disrupts the binding between the drug conjugate and the second member of the affinity binding pair to result in drug release.

The present application also includes a use of a formulation of the application for release of a drug in a subject. The present application also includes a method of releasing a drug in a subject in need thereof comprising administering a effective amount of a formulation of the application to the subject. In some embodiments, the release of the drug is sustained over a desired period of time.

The present application also includes a kit for drug release comprising
  (a) a drug conjugate comprising a drug bound to a first member of an affinity binding pair;
  (b) a second member of the affinity binding pair, wherein the drug conjugate reversibly binds to the second member of the affinity binding pair to form a complex; and
  (c) a competitive binding compound that disrupts the binding between the drug conjugate and the second member of the affinity binding pair to result in drug release.

In one embodiment, the formulation comprises a two-step system involving a high affinity interaction between the drug conjugate and a compound, and the introduction of a second compound with a higher affinity to the drug conjugate to allow for drug release. The properties of the second compound can be modified to allow for sustained drug release for example, for a few months to over a year. Several delivery methods for the formulations are described that include the incorporation of hydrogels, microparticles and nanoparticles.

In another embodiment, the drug release formulation can be utilized based on desthiobiotin, streptavidin and biotin derivative interactions.

In some embodiments, the present application includes a method for delivering a drug to a patient using a sustained two-step affinity based drug release system comprising:
  (a) a drug conjugate with high affinity for a first compound; and
  (b) a second compound with higher affinity for the drug conjugate compared to the first compound, such that the second compound displaces the first compound and results in drug release;
wherein the delivery mechanism and/or concentration of the second compound in the soluble phase controls drug release.

BRIEF DESCRIPTION OF THE DRAWINGS

Embodiments of the application are shown in more detail by the reference to the drawings in which.

Native PAGE showing the fluorescently labelled streptavidin-Avastin® (bevacizumab) conjugate, Avastin® (bevacizumab) and streptavidin.

Figure 11:
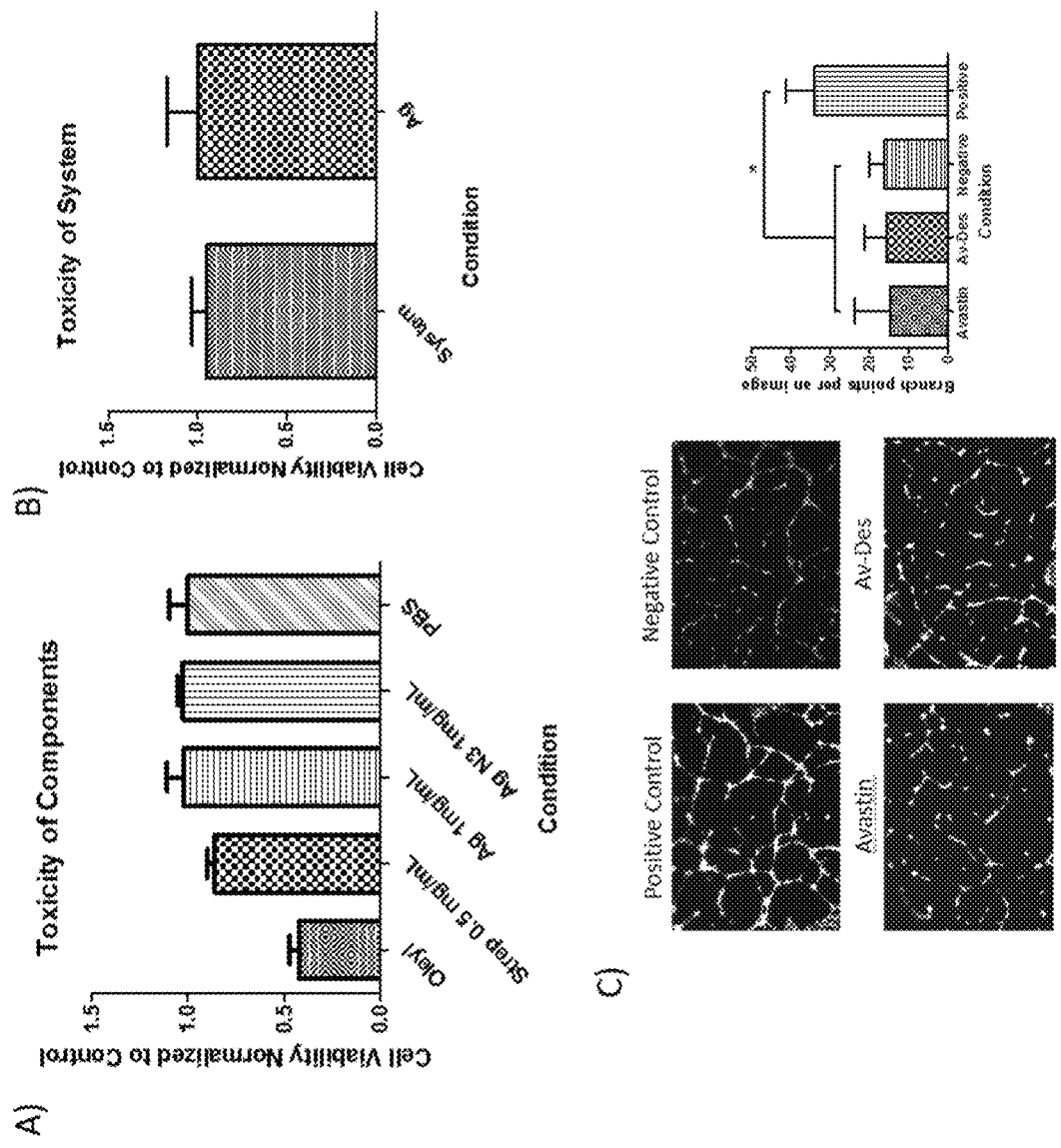

FIG. 11 shows A) the results of an MTS assay assessing cell toxicity of components of the exemplary drug release system in Example 2 towards HUVECS. The results show minimal toxicity for most components except the solid suspension of oleylbiotin on its own. B) the results of an MTS assay a whole exemplary system incorporated together comparing cell viabilities of HUVECS when compared to a neutral agarose hydrogel. The entire system with oleylbiotin was shown to be non-cytotoxic. C) the results of an HUVEC tube formation assay demonstrating that exemplary modified Avastin® (bevacizumab)-desthiobiotin remains bioactive by inhibiting VEGF-165a induced tube formation.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a compound" should be understood to present certain aspects with one substance or two or more additional substances.

In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "drug" is a well-known term used in the art to refer to any therapeutic agent or combination of agents that is administered or used in human or animal subjects to treat a disease, disorder or condition.

The term "drug conjugate" as used herein refers to a drug covalently bound to one member of a binding complex.

The term "binding complex" as used herein refers to a complex of at least two molecules that have a strong affinity for each other.

The term "hydrogels" as used herein refers to any three-dimensional, cross-linked networks of water-soluble polymers. Hydrogels can be made from virtually any water-soluble polymer, encompassing a wide range of chemical compositions and bulk physical properties. Furthermore, hydrogels can be formulated in a variety of physical forms, including slabs, microparticles, nanoparticles, coatings, and films.

"Pharmaceutical formulation" refers to a composition of matter or a combination of compositions of matter for pharmaceutical use and therefore is pharmaceutically acceptable.

The term "pharmaceutically acceptable" means compatible with the treatment of animals, in particular, humans.

The term "effective amount" as used herein means an amount sufficient to achieve the desired result and accordingly will depend on the ingredient and its desired result. Nonetheless, once the desired effect is known, determining the effective amount is within the skill of a person skilled in the art.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, prevention of disease spread, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. Treatment methods comprise administering to a subject a therapeutically effective amount of a drug and optionally consists of a single administration, or alternatively comprises a series of applications. The length of the treatment period depends on a variety of factors, such as the severity of the condition, the age of the patient, the concentration of active ingredient or agent, the activity of the compositions described herein, and/or a combination thereof. The treatment period may also comprise cycles. Patients may be treated with more than one cycle, for example, at least two, three, four or five cycles. It will also be appreciated that the effective dosage of the drug used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "subject" as used herein includes all members of the animal kingdom, including mammals, and suitably refers to humans.

II. Detailed Description

Figure 3:
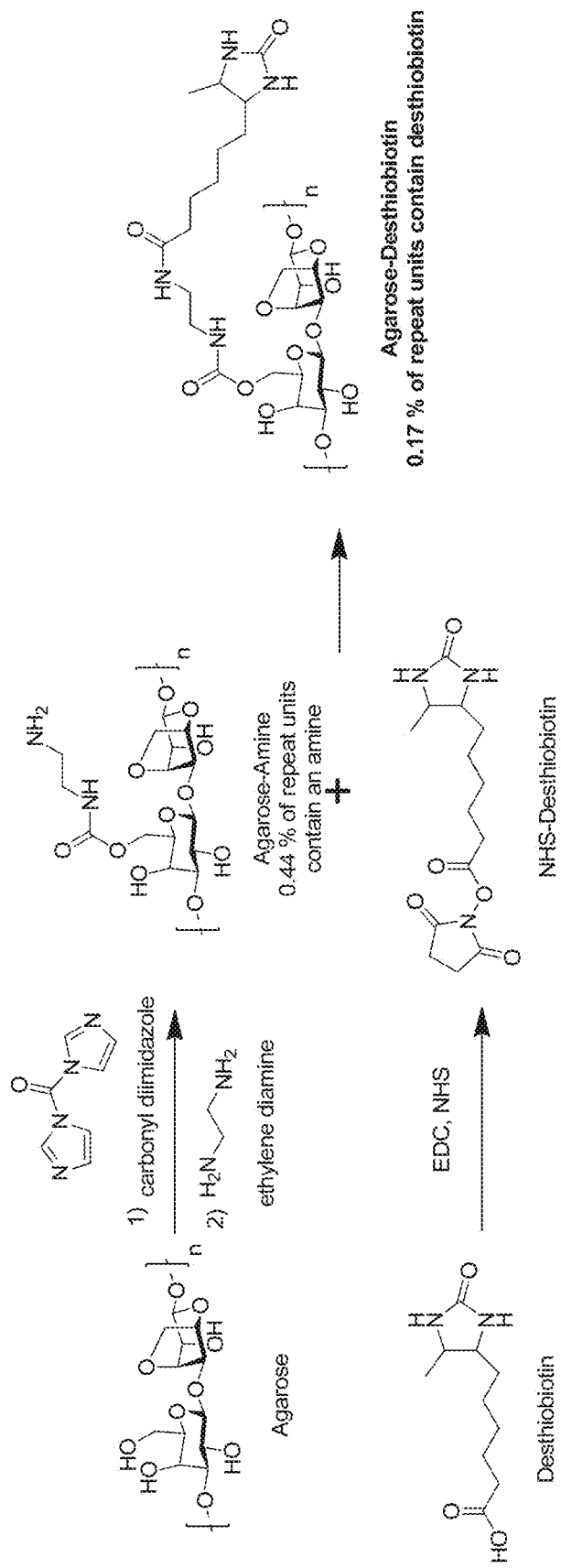
FIG. 3 shows the synthesis of agarose-desthiobiotin conjugates in an exemplary embodiment of the application.

An agarose hydrogel was modified with a desthiobiotin moiety via carbodiimide chemistry (see FIG. 3). Streptavidin was conjugated to a drug (e.g. an antibody) via strain promoted azide alkyne cycloaddition (SPAAC). The streptavidin-drug conjugate was introduced to the delivery system, and was immobilized to the polymer backbone due to the high but reversible affinity of streptavidin and desthiobiotin. A sparingly soluble biotin derivative was then introduced, the soluble fraction of this derivative displaces the streptavidin from the backbone due to a higher affinity for streptavidin, releasing the drug out of the hydrogel. This thus creates a two step affinity based mechanism where the rate of release of the drug conjugate is governed by the solubilisation of the sparingly soluble biotin derivative as well as the binding and unbinding kinetics of the affinity interaction. In an alternative embodiment, agarose was modified to contain an azide moiety to which a DBCO modified streptavidin is conjugated via SPAAC and the antibody drug was modified with desthiobiotin. When introduced to the streptavidin modified agarose, the antibody is immobilized onto the polymer backbone due to the high affinity of desthiobiotin to streptavidin. Similar to the first embodiment, a sparingly soluble biotin derivative is introduced to the system, where the soluble fraction irreversibly displaces the drug from the polymer backbone due to biotin's higher affinity for streptavidin, releasing the drug and resulting in a drug delivery system where the rate of release is dictated once again by the binding kinetics of the desthiobiotin and biotin. A person skilled in the art would appreciate that this novel two step method for drug release can be applied to any affinity binding pair of molecules an adapt the method accordingly.

Accordingly the present application includes a pharmaceutical drug release formulation comprising:

(a) a drug conjugate comprising a drug bound to a first member of an affinity binding pair;

(b) a second member of the affinity binding pair, wherein the drug conjugate reversibly binds to the second member of the affinity binding pair to form a complex; and (c) a competitive binding compound that disrupts the binding between the drug conjugate and the second member of the affinity binding pair to result in drug release.

In some embodiments, at least one of the first and second members of the affinity binding pair are bound to or encapsulated in a supporting matrix. In some embodiments, the second member of the affinity binding pair is covalently bound to the supporting matrix. In some embodiments, the supporting matrix is selected from one or more of a hydrogel, nanoparticle and microparticle. In some embodiments, the supporting matrix is a hydrogel. In some embodiments, the supporting matrix comprises one or more of agarose, dextran, PEG and PEG-derived polymers (such as PEGMA). In some embodiments, the supporting matrix comprises agarose.

In some embodiments the affinity binding pair is based on the biotin-streptavidin interaction.

In some embodiments, the first member of the affinity binding pair is strepavidin, the second member of the affinity binding pair is desthiobiotin or iminobiotin, suitably desthiobiotin, and the competitive binding compound is selected from biotin and a biotin derivative. In some embodiments, the biotin derivative is less soluble in aqueous solution than biotin. In some embodiments, the biotin derivative is selected to have a solubility in aqueous solutions to adjust the rate of release of the drug to a desired value.

In some embodiments, the biotin derivative is a hydrophobic biotin derivative. In some embodiments, the hydrophobic biotin derivative is selected from tert-butyl biotin and oleyl-biotin.

In some embodiments, the first member of the affinity binding pair is desthiobiotin, the second member of the affinity binding pair is streptavidin, the competitive binding compound is selected from biotin and a biotin derivative.

In some embodiments, the competitive binding compound is selected from biotin and a hydrophobic biotin derivative. In some embodiments, the hydrophobic biotin derivative is a long chain biotin derivative of the formula:

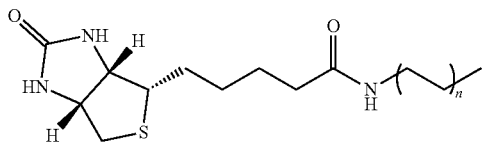

wherein, n is an integer between 1 and 20.

In some embodiments, the drug is a macromolecule. In some embodiments, the macromolecule is a protein, peptide, antibody or nucleic acid. In some embodiments, the drug is Avastin® (bevacizumab). In some embodiments, the drug is present in the formulation in an effective amount.

In some embodiments, the competitive binding compound is comprised in the supporting matrix in a form selected from insoluble pellets and insoluble particles.

Is some embodiments, the competitive binding compound is comprised in a separate composition that is added to the drug conjugate-second member of the affinity binding pair complex prior to administration to or use in a subject. In some embodiments, the separate composition for the competitive binding compound comprises one or more competitive binding compounds entrapped or encapsulated in a matrix. In some embodiments, the separate composition for the competitive binding compound is in the form of pellets or microparticles. In some embodiments, the matrix for the competitive binding compound is the same as that for the complex. In some embodiments, the separate composition for the competitive binding compound comprises one or more competitive binding compounds suspended or dissolved in a pharmaceutically acceptable solvent. In some embodiments, the rate of release of the one or more competitive binding compounds from the separate composition controls the rate of release of the drug.

In some embodiments, the competitive binding compound has a solubility in the supporting matrix or in aqueous solution that controls interaction of the competitive binding compound with the complex and the interaction of the competitive binding compound with the complex controls the release of the drug.

In some embodiments, the formulation of the application is formulated for administration by injection or by implantation. In some embodiments, the formulation further comprises pharmaceutically acceptable excipients, diluents and/or additives.

The present application also includes a use of a formulation of the application for release of the drug in a subject.

The present application also includes a method for release of the drug in a subject in need thereof comprising administering an effective amount of a formulation of the application to the subject.

In some embodiments, the release of the drug is sustained over a desired period of time. In some embodiments, the desired period of time is about 1 day to about 1 year, and any time period in between. In some embodiments, the desired period of time is about 1 month to about 10 months or about 3 months to about 8 months.

In some embodiments, the formulation is for administration of a drug for treatment of the eye, for example, for treatment of retinal diseases or disorders.

In some embodiments, the formulation is for administration of a drug for treatment of a cancer.

In some embodiments, the formulation comprises an effective amount of the drug for treatment.

III. Examples

The following example illustrates the scope of the application. Specific elements of the examples are for descriptive purposes only and are not intended to limit the scope of the application. Those skilled in the art could utilize comparable materials that are within the scope of the application.

The following abbreviations are used throughout the application:
DBCO: dibenzocyclooctyne
SDS PAGE: sodium dodecyl sulfate polyacrylamide gel electrophoresis
DMSO: dimethylsulfoxide
CDI: carbonyldiimidazole
MWCO: molecular weight cut-off
h: hour(s)
EDAC HCl or EDC HCl: 1-ethyl-3-(3-dimethylaminopropyl)carbodiimide, hydrochloride
NHS: N-hydroxysuccinimide
DMF: dimethylformamide
TEA: triethylamine
DCM: dichloromethane
PEG: polyethyleneglycol
PBS: phosphate buffered saline
FPLC: fast protein liquid chromatography
SAv: streptavidin
SPAAC: strain promoted azide alkyne cycloaddition
UV Vis: ultra-violet visable
Cy5: cyanine 5
PEGMA: poly(ethylene glycol) methyacrylate Example 1: Desthiobiotin Immobilized to Hydrogel with a Streptavidin Modified Drug Experimental Methods and Procedures
Agarose-Desthiobiotin Synthesis—1

1 g of agarose was dissolved into 50 mL of DMSO. 92 mg of CDI and 600 uL of trimethylamine were added and allowed to react for 2 h at room temperature under nitrogen. An additional 600 uL of triethylamine along with 198 uL of ethylenediamine were added to the reaction mixture and the mixture was stirred overnight under nitrogen at room temperature. The solution was then dialyzed against water for 3 days (MWCO 3500) and lyophilized, obtaining aminated agarose (see FIG. 3).

Separately, 120 mg desthiobiotin, 325 mg EDAC HCl and 200 mg N-hydroxysuccinimide (NHS) were dissolved in 10 mL DMF and reacted under nitrogen overnight. The reaction mixture was then poured into a solution of 2% aminated agarose in dissolved in DMSO. It was allowed to react over 2 days at room temperature under nitrogen. 200 mL of warm water was then poured into the mixture and dialyzed over 3 days (MWCO 3500) against water, then lyophilized, yielding desthiobiotin modified agarose (Ag-D) (see FIG. 3).
Agarose-Desthiobiotin Synthesis—2

500 mg of agarose was reacted with 86 mg of CDI for 1 h in 50 mL DMSO under nitrogen. 106 uL of ethylenediamine and 296 uL of TEA was added to the reaction and reacted overnight under nitrogen. The reaction mixture was then diluted to 2 mg/mL with water and dialyzed against water with 12 k MWCO membrane for 3 days, with 6 water exchanges. Product was lyophilized and used for the next step.

Separately, 120 mg desthiobiotin, 325 mg EDC HCl and 200 mg NHS were dissolved in 20 mL DMF and reacted under nitrogen overnight. 450 mg of agarose amine was dissolved in 30 mL of DMSO under nitrogen and the desthiobiotin reaction mixture was then added to the agarose-amine. The reaction occurred overnight and then was diluted to 2 mg/mL with water and dialyzed against water with 12 k MWCO membrane for 3 days, with 6 water exchanges. The product was lyophilized.
Agarose Wash In order to remove excess desthiobiotin, Ag-D was dissolved in $dH_2O$ at 0.7 wt %, poured into petri dishes and gelled at 4° C. The dish was then submerged in 5 L of $dH_2O$ for 2 weeks. The gel was scraped off the dish and lyophilized, yielding clean Ag-D.
Biotin Modification—1

Figure 4:
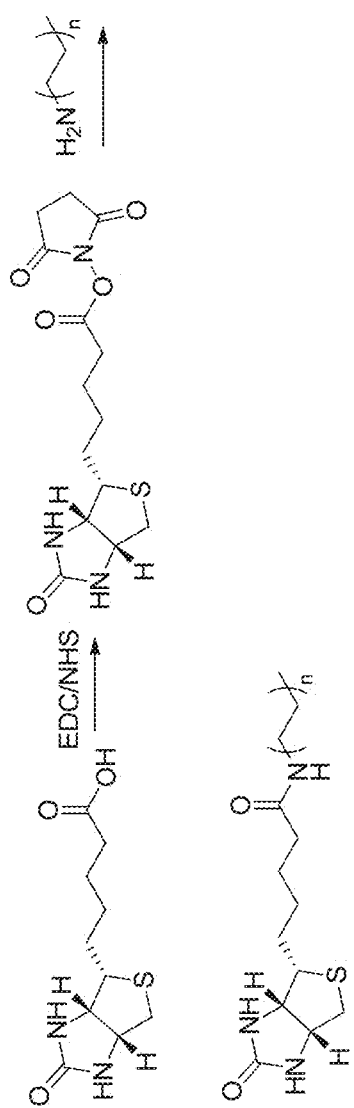
FIG. 4 shows the synthesis of hydrophobic biotin derivatives using EDC/NHS chemistry in an exemplary embodiment of the application. Any hydrophobic molecule containing a primary amine can be coupled to the carboxylic acid of biotin.

75 mg of biotin, 176 mg EDAC HCl, 106 mg NHS was dissolved in 5 mL of dry DMF and reacted under nitrogen overnight. 3 molar equivalents of a long chain aliphatic amine (e.g., oleyl-amine, N-Boc-1,6-hexanediamine) along with 280 uL trimethylamine (see FIG. 4). Upon the addition of these reagents, a precipitate was formed. The mixture reacted overnight at room temperature. 0.25M $NaCO_3$ solution was then added to the reaction mixture and the precipitate was collected. The precipitate was repeatedly washed with $dH_2O$, and depending on the identity of the amine, the precipitate would be redissolved and purified through FLASH chromatography using a 90:10 DCM:MeOH gradient.
Biotin Modification—2

100 mg of biotin was dissolved in 5 mL DMF. 118 mg EDC HCl and 71 mg NHS was then added and allowed to react overnight under nitrogen. 3 molar equivalents of the corresponding aliphatic amine was then added and allowed to react overnight at room temperature. DMF was then dried via rotary evaporation and product was then washed repeatedly in water and crystallized in methanol.
Biotin Solubilities The solubility of the biotin derivatives was investigated since biotin solubilization in the hydrogel is a factor for drug release. Biotin derivatives were added to water until insoluble particles were seen, insoluble particles were then removed by filtration and a HABA (4'-hydroxyazobenzene-2-carboxylic acid) avidin displacement assay was used to quantify the levels of soluble biotin in solution. The oleyl derivative showed a significant but small soluble fraction at 1.21 uM whereas both the octyl and the Boc derivatives showed a soluble concentration about 100 times greater (see FIGS. 5A and 5B). The hexadecyl derivative showed no measurable solubility in water. These results were consistent to what is seen in the release profiles (FIG. 5C), since higher solubilities should result in faster release. However, as the hexadecyl seems to achieve some degree of release, this derivative is not completely insoluble in water.
Streptavidin-Avastin® (Bevacizumab) Conjugate Synthesis 5 mg/mL streptavidin was reacted with 10 molar equivalents of DBCO NHS ester overnight in PBS. Similarly 5 mg/mL Avastin® (bevacizumab) was reacted with an azide NHS ester overnight in PBS. Both were dialyzed against PBS pH 7.4 for 2 days using a 13-16 k MWCO membrane. The reaction mixture was then filtered via a syringe filter to remove residual DBCO. Avastin® (bevacizumab) was further reacted with 10 molar equivalents of Alexa Fluor 488 NHS ester and also purified via dialysis. 2 fold molar excess of strep-DBCO was then reacted with Avastin® (bevacizumab)-$N_3$-488 overnight in PBS and SDS PAGE and Native PAGE were used to confirm the presence of the conjugate.

Release Study—Fluorescent Streptavidin

Figure 5:
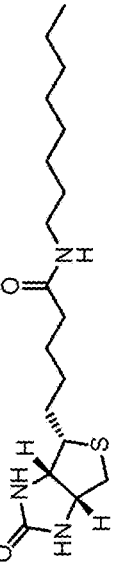
FIG. 5 shows A) biotin derivatives synthesized with different aliphatic chains conjugated resulting in decrease in solubility in exemplary embodiments of the application; B) solubility of biotins found using a HABA streptavidin displacement assay; c) cumulative release of Streptavidin-488 using the system from Example 1 (desthiobiotin immobilized to the hydrogel with a streptavidin modified drug), demonstrating how a decrease in the biotin solubility results in an attenuation the burst release of fluorescently labelled streptavidin as well as a sustained release of the fluorescent protein over a number of days.
Figure 5:
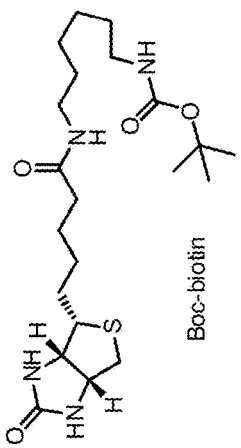
Figure 5:
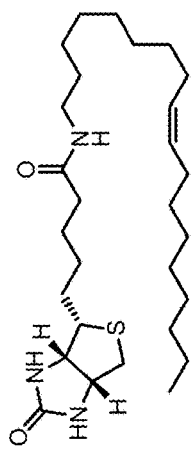
Figure 5:
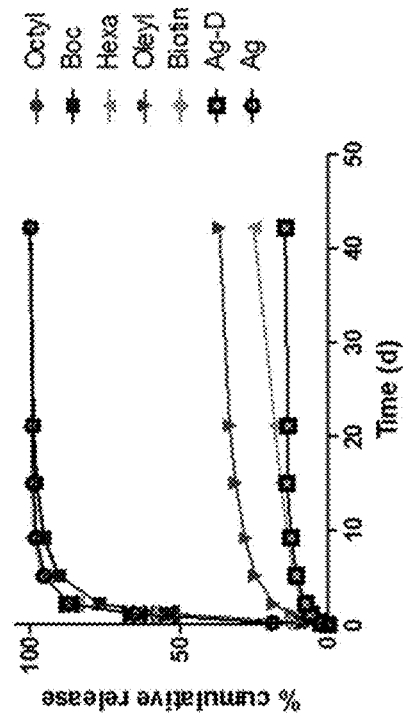
Figure 5:
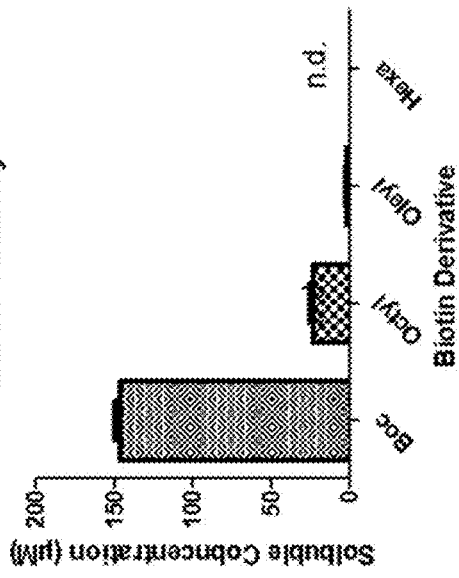
Figure 6:
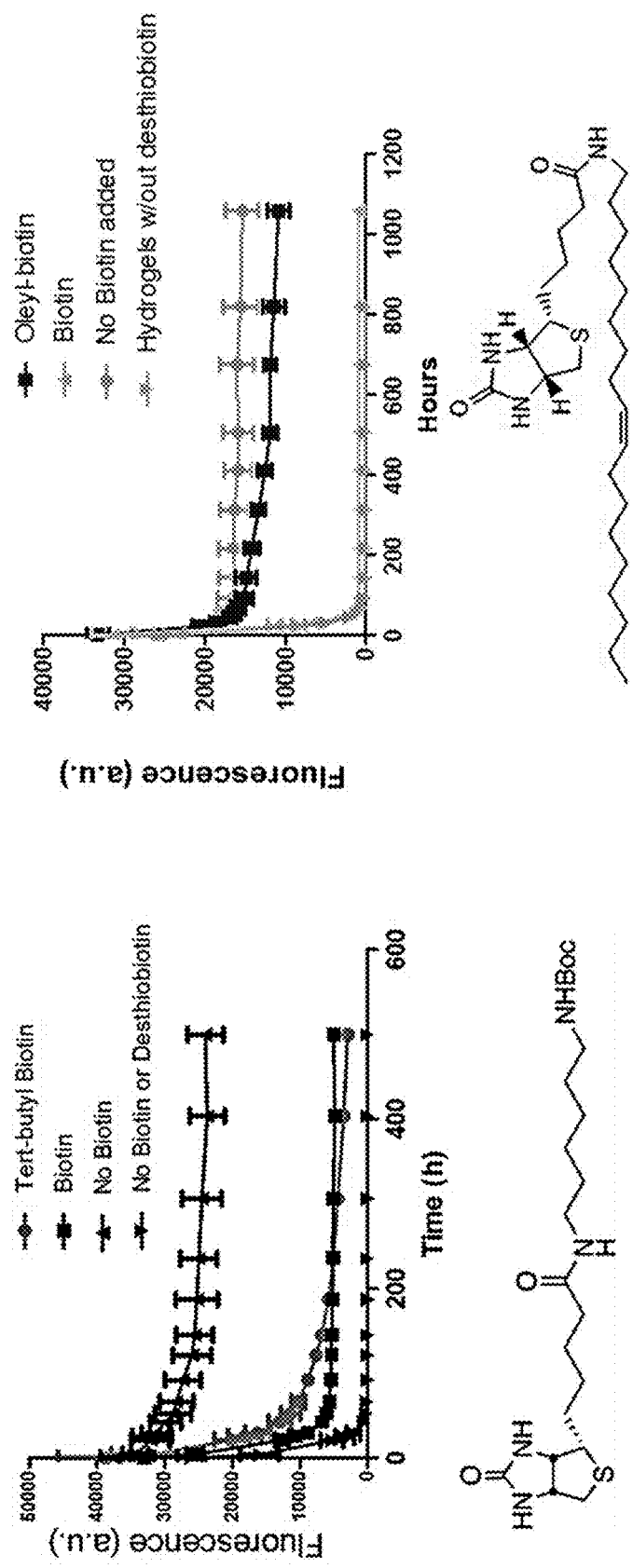
FIG. 6 shows controlled release of fluorescent streptavidin from exemplary desthiobiotin hydrogels using exemplary hydrophobic tert-butyl and oleyl-biotin derivatives by following the fluorescence of the hydrogel.

Ag-D was dissolved in 0.1M PBS at 2 wt %, Alexa-Fluor 488 streptavidin was subsequently added and the mixture was incubated at 37° C. for 2 h. Solid insoluble biotin particles were suspended in 0.1M PBS buffer and were mixed with the Ag-D streptavidin mixture in a black opaque 96 well plate, resulting in a final gel composition of 1 wt % Ag-D, 4 mg/mL or equivalent molar concentration of insoluble biotin derivative, and 0.1 mg/mL streptavidin. Gels were cured at 4 C for 20 min to 1 hr and initial fluorescent readings of the gel were taken. 200 uL of PBS was subsequently dispensed overtop of the gels and collected and replenished at specific time intervals. The loss of fluorescence as well as the released fluorescent streptavidin was measured at specific time points (FIGS. 5B and 6).

Results

Synthesis and Characterization of Agarose-Desthiobiotin

To covalently conjugate desthiobiotin to agarose, amine-functionalized agarose (agarose-amine) and N-hydroxysuccinimide desthiobiotin (NHS-desthiobiotin) were first synthesized. Agarose was reacted with carbonyl diimidazole (CDI) to activate the agarose hydroxyl groups, which were then reacted with a large excess of ethylene diamine. After dialysis, agarose-amine was reacted with NHS-desthiobiotin to yield agarose-desthiobiotin (Ag-D) (FIG. 3). The degree of amine and desthiobiotin functionalization of agarose was determined using a fluorescamine assay where N-(2-aminoethyl) acetamide was the amine standard in the calibration curve. Agarose-amine was determined to have an amine substitution rate of 4.4±0.3 μmol of amines per mmol of agarose repeat units (mean±standard deviation, n=3). Agarose-desthiobiotin retained 3.0±0.5 μmol of amines per mmol of agarose (mean±standard deviation, n=3), which is significantly different from agarose-amine (unpaired t test, p<0.05). Since the decrease in primary amine content is due to desthiobiotin conjugation, a desthiobiotin substitution rate of 1.4±0.6 μmol of desthiobiotin per mmol of agarose subunit (mean±standard deviation n=3) was estimated. The Thermo Scientific Fluorescence Biotin Quantitation assay was used to confirm desthiobiotin content in agarose using a desthiobiotin calibration curve, which yielded a substitution rate of 1.7±0.5 μmol desthiobiotin per mmol of agarose subunit (mean±standard deviation n=3), which was not significantly different from the fluorescamine assay estimate (unpaired t test, p<0.05). Therefore, the desthiobiotin concentration of 55 μM in 1 wt % hydrogel was used for binding studies. The degree of desthiobiotin within the hydrogel can be increased by simply changing the reaction conditions.

Synthesis of Hydrophobic Biotins

Hydrophobic biotins are synthesized by reacting biotin with hydrophobic amine molecules (FIG. 4). The carboxylic acid of biotin is activated with EDC/NHS, which was then reacted directly with a primary or secondary amine containing molecules. Hydrophobicity of the biotin derivative was varied by changing the amine molecule.

Stability of Immobilized Streptavidin with Agarose-Desthiobiotin Gels

Figure 7:
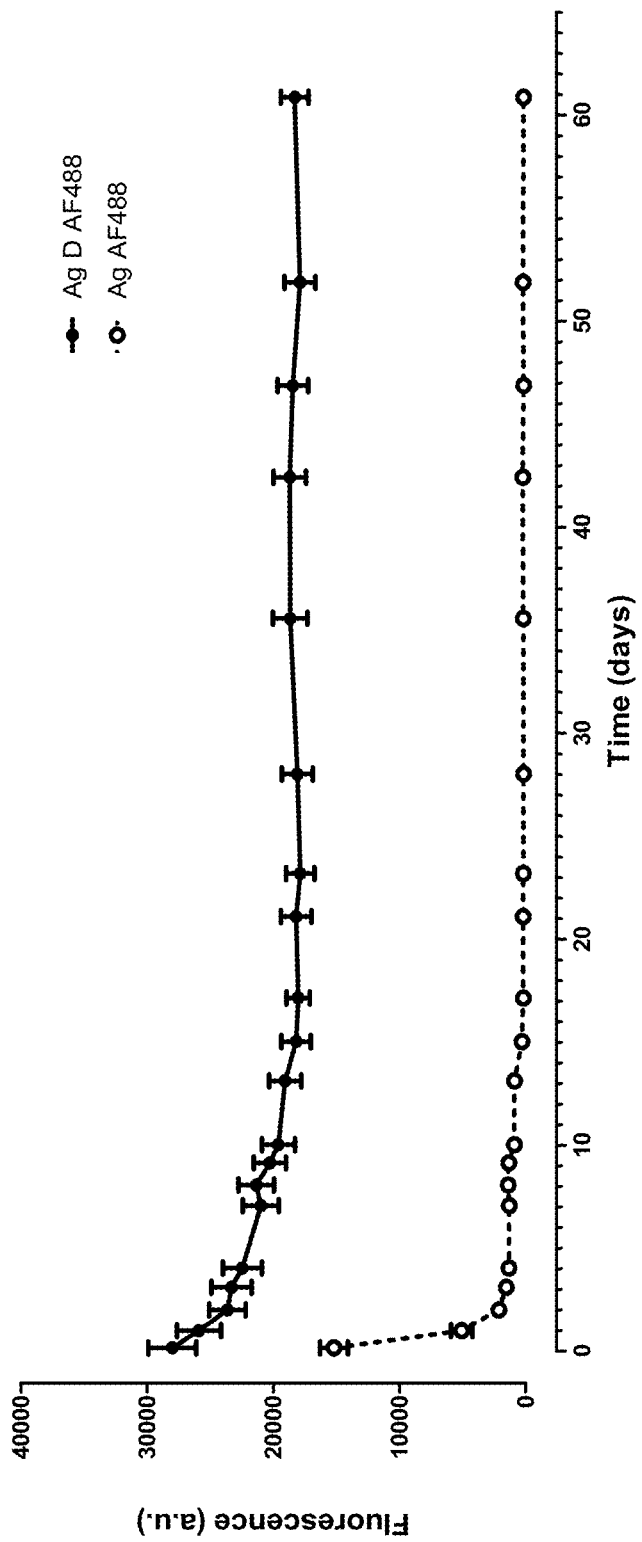
FIG. 7 shows the stability of the desthiobiotin-streptavidin interaction over time in agarose hydrogels in an exemplary embodiment of the application. The solid line represents streptavidin release from desthiobiotin containing agarose hydrogels. The dashed line represents streptavidin release from agarose hydrogels that do not contain desthiobiotin.

Fluorescent streptavidin immobilized in agarose-desthiobiotin gels remains stable in the absence of biotin (FIG. 7). Streptavidin remains immobilized in agarose hydrogels for at least 60 days after an initial burst release due to excess streptavidin (solid line). Fluorescent streptavidin rapidly diffuses from agarose hydrogels without desthiobiotin (dashed line). Without biotin present, no streptavidin is released. Therefore, the agarose-desthiobiotin eliminates any passive diffusion of fluorescent streptavidins from the gel, and can be controlled by the soluble concentration of biotin.

Sparingly Soluble Biotin Derivatives Control the Release of Streptavidin Conjugates It has been demonstrated that the rate of release of fluorescent streptavidins can be controlled by encapsulating pellets of sparingly soluble biotin derivatives within the hydrogels. This method limits the amount of soluble biotin within the hydrogel, which can be controlled by varying the solubility and hydrophobicity of the biotin derivative. Soluble biotin will displace desthiobiotin from the streptavidin binding pocket since biotin has a higher affinity than desthiobiotin for streptavidin. The biotin-streptavidin complex will then diffuse from the hydrogel.

The effect of 3 different biotin derivatives was compared: 1) Biotin 2) Tert-butyl biotin and 3) Oleyl-biotin, along with controls (FIG. 6). Samples without biotin showed an initial small burst release, due to excess streptavidin, followed by no release. Hydrogels without desthiobiotin showed a rapid release of streptavidin, as expected. Unmodified biotin has the highest solubility and therefore, results in the most rapid release of fluorescent streptavidin from the hydrogel. Tert-butyl biotin is more hydrophobic and less soluble than biotin, and resulted in a slower release of fluorescent streptavidin from the hydrogel when compared to biotin. The most hydrophobic and least soluble biotin, oleyl-biotin, resulted in the slowest and longest release of streptavidin. Therefore, the release of streptavidin conjugates can be tailored by controlling the soluble concentration of biotin within the hydrogel. This can be accomplished by synthesizing hydrophobic biotins, as described herein, or using particles to slowly release biotin over time.

Figure 8:
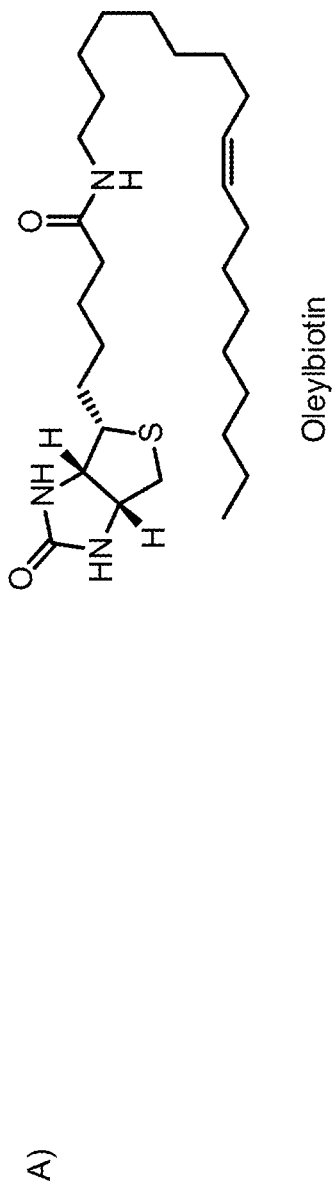
FIG. 8 shows A) the structure of oleylbiotin used for the streptavidin release assay; B) the release of fluorescently labelled streptavidin using oleylbiotin at various concentrations. This experiment demonstrated that the concentration of oleylbiotin can modulate the release of streptavidin for at least 150 days (using the system from Example 1); and C) the transparency of agarose hydrogels with a solid suspension of oleylbiotins at different concentrations. Oleylbiotin concentrations of 80 µM or less did not decrease the transparency of agarose gels.
Figure 8:
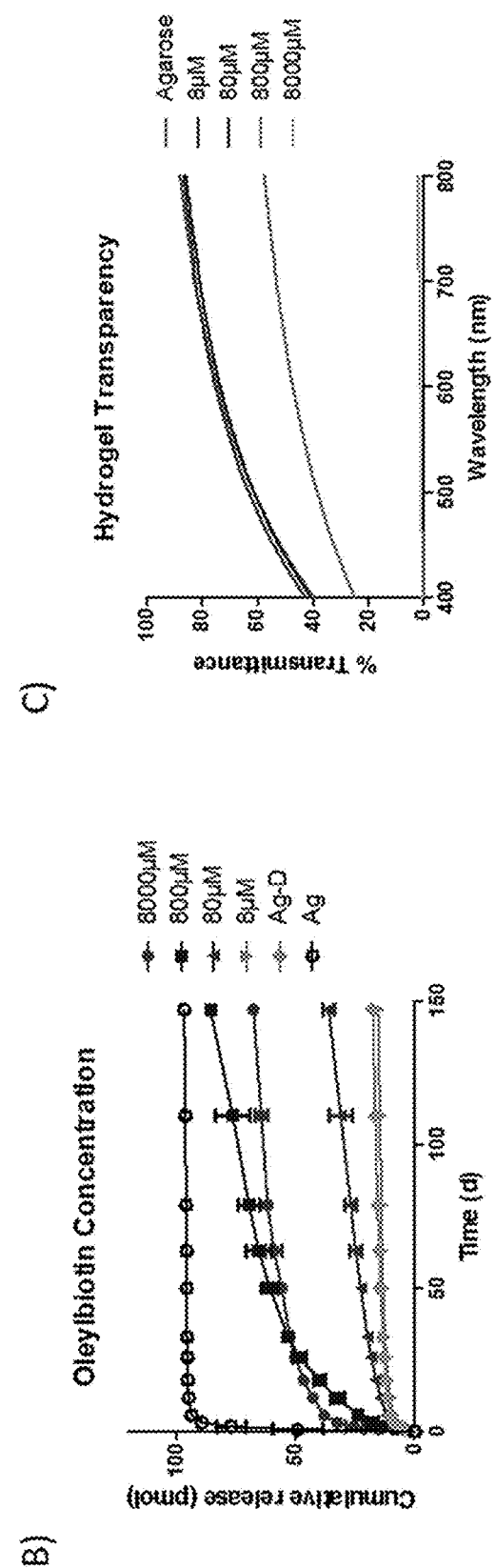

Extrapolation of preliminary experiments with oleyl-biotin indicate release for >100 days with wild-type streptavidin (FIG. 8). Decreasing the desthiobition dissociation constant using known variants of streptavidins will increase total release time by a factor of ~10. Therefore, biotins less hydrophobic than oleyl-biotin may be used and a 1 year release rate still achieved. Although, it is optimal for the biotins to be sufficiently hydrophobic to remain as an insoluble pellet within the hydrogel for the duration of drug release. The optimal system will have a desthiobiotin dissociation rate constant and a hydrophobic biotin which meets all the criteria.

The results in this Example show, that the drug delivery system of the present application is capable in sustaining the release of macromolecular drugs such as proteins over many months, and that the rate of release is largely due to the two step release mechanism where the solubility of the competitive binder, in this case biotin, largely dictates the release of the protein.

Example 2: Streptavidin Immobilized to the Hydrogel with a Desthiobiotin Modified Drug Agarose Azide Synthesis 500 mg of agarose was reacted with 86 mg of CDI for 2 h in 10 mL DMSO under nitrogen. 106 uL of ethylenediamine and 296 uL of TEA was added to the reaction and reacted overnight under nitrogen. The reaction mixture was then diluted to 2 mg/mL with water and dialyzed against water with 12 k MWCO membrane for 3 days, with 6 water exchanges. Product was lyophilized and used for the next step. Yield: 409 mg. 409 mg of Agarose amine was then reacted with 150 uL of 6-azidohexanol NHS carbonate in 40 mL of DMSO overnight under nitrogen. Reaction mixture was then diluted with water and dialyzed against water for 3 days. Product was lyophilized and stored at 4 C (see FIG. 9).

Synthesis of DBCO-Streptavidin 5 mg of streptavidin was dissolved in 1 mL of pH 8.5 PBS buffer and reacted with 10 molar equivalents of DBCO-PEG4-NHS ester for 2 h at room temperature. The reaction mixture was then purified via size exclusion chromatography using a Superdex HiLoad 16/600 column and a shimadzu FPLC. Fractions were collected and further reacted with Alexa-fluor 647 NHS ester in pH 8.5 PBS buffer and purified in a similar fashion. Streptavidin modification and DBCO reactivity was confirmed via SDS PAGE, reacting with an excess of Cy5-$N_3$ dye. Degree of conjugation was measured via UV Vis, using the known extinction coefficient of DBCO at 309 nm of 12 000 $M^{-1}$ $cm^{-1}$ (see FIG. 9).

Avastin® (Bevacizumab) Modification 5 mg/mL Avastin® (bevacizumab) in pH 8.5 was reacted with 10 molar equivalents of desthiobiotin NHS ester. Avastin® (bevacizumab) was purified via size exclusion chromatography as per described above. Separately, Avastin® (bevacizumab) was modified with biotin in a similar manner. Degree of conjugation was measured via a HABA streptavidin assay, using known extinction coefficients.

Streptavidin Conjugation

Figure 9:
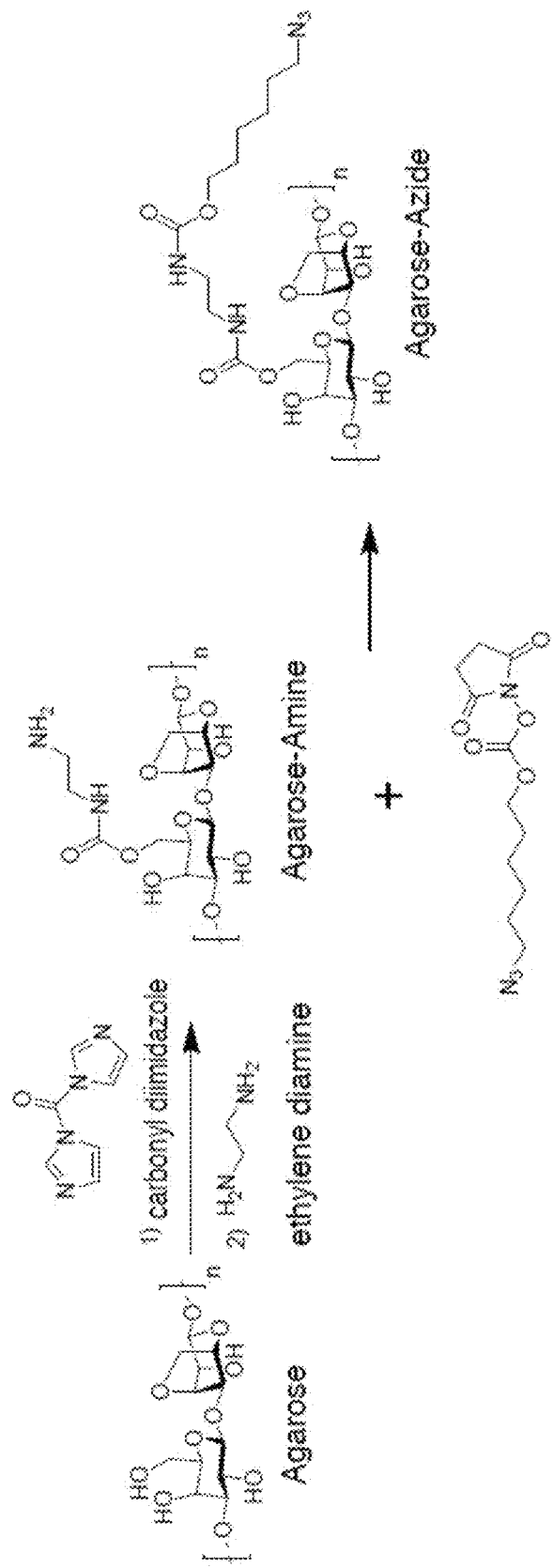
FIG. 9 shows a synthetic scheme for the modification of agarose with an azide moiety in an exemplary embodiment of the application.
Figure 10:
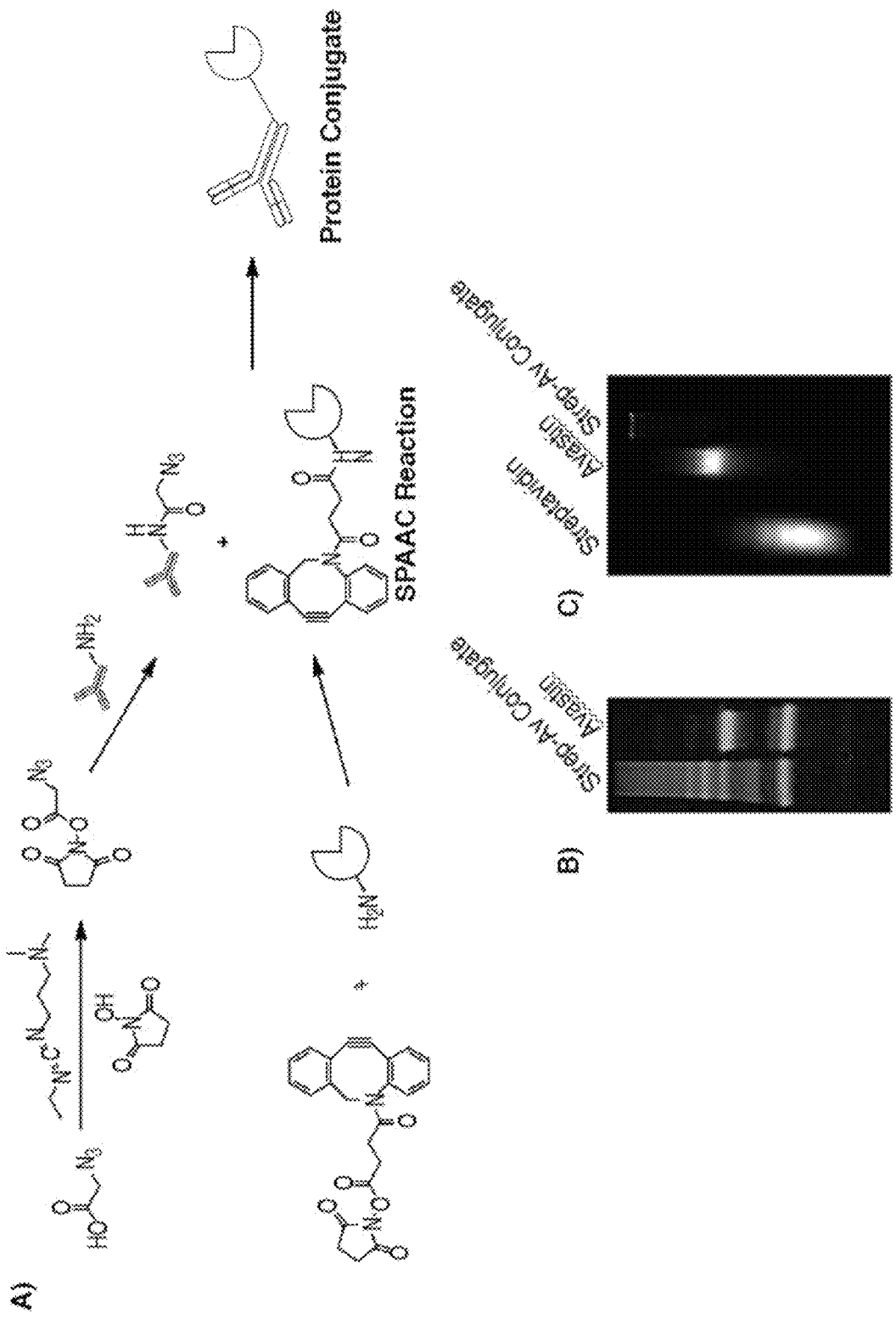
FIG. 10 shows an exemplary synthesis of a streptavidin-Avastin® (bevacizumab) conjugate. A) Schematic of the conjugation scheme using azide-modified streptavidin and DBCO modified streptavidin. B) SDS PAGE gel showing successful conjugation of streptavidin and Avastin® (bevacizumab) due to increase in molecular weight bands. C)

Agarose-azide (Ag—$N_3$) was dissolved in PBS pH 7.4 and incubated with different concentrations of streptavidin-DBCO-647 (SAv-DBCO-647) overnight. A corresponding amount of PBS was then added to the mixture in order to obtain a final agarose concentration of 1 wt %. 60 uL gels were plated onto a black opaque 96 well plate and cured for 30 min at 4 C. Gels were immersed in PBS and remaining fluorescence in the gels was tracked (FIG. 9).

Results

Figure 1:
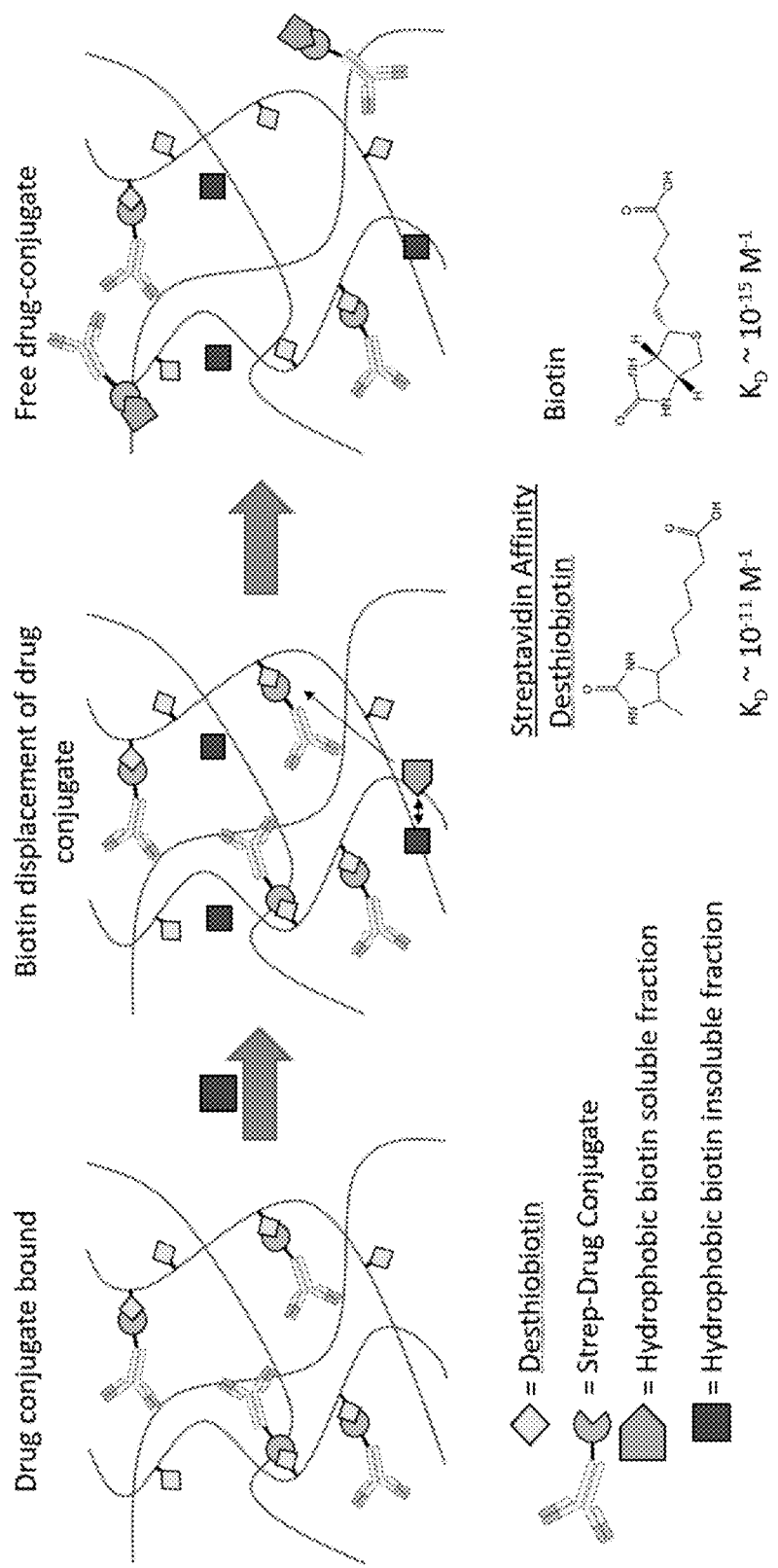
FIG. 1 shows a schematic representing the exemplary release system described in Example 1 (desthiobiotin immobilized to the hydrogel with a streptavidin modified drug). A streptavidin-drug conjugate is first loaded onto the hydrogel backbone by binding desthiobiotin. The insoluble biotin derivative is subsequently introduced, resulting in a soluble fraction of the biotin derivatives that displaces the streptavidin-drug conjugate from the polymer backbone, thus releasing the drug. The solubility of the biotin derivative controls the release rate.
Figure 2:
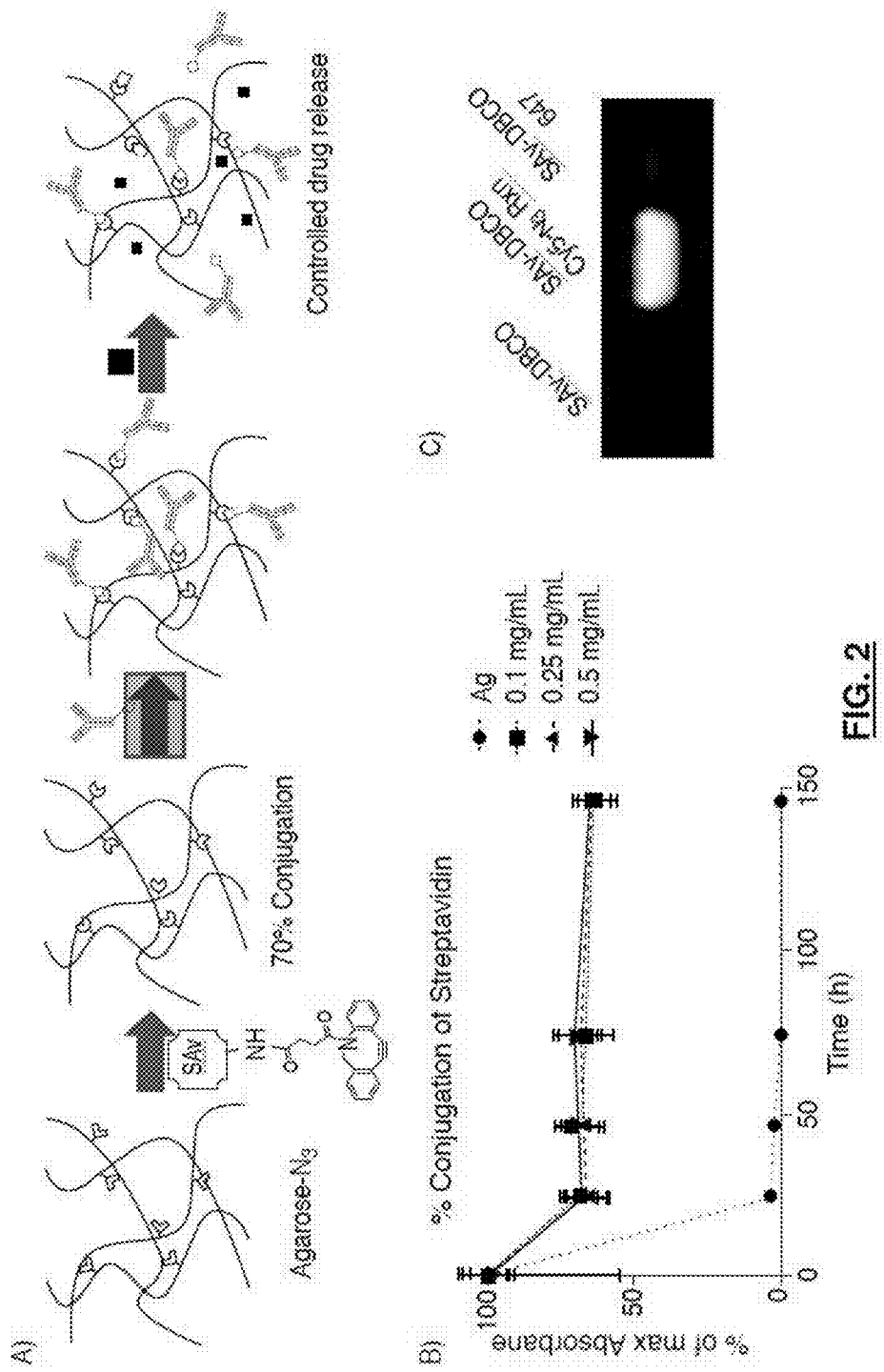
FIG. 2 A) shows a schematic representing the exemplary release system described in Example 2 (streptavidin immobilized in hydrogel with a desthiobiotin modified drug). Agarose-$N_3$ is first conjugated to Streptavidin-DBCO and the desthiobiotin modified antibody is then added to the mixture and immobilized onto the backbone of the polymer. Insoluble biotin is then added and the soluble portion displaces the antibody from the backbone and controls the release the drug (e.g. antibody). B) shows the conjugation efficiency of Streptavidin-DBCO-647 onto the backbone of agarose hydrogels remains stable over a number of days over various concentration ranges with 70% conjugation efficiency. C) shows fluorescent SDS PAGE illustrating that the DBCO moiety of the modified streptavidin is reactive towards a Cy5-$N_3$ dye.

Here, the components of the drug delivery system described in Example 1 are reversed, resulting in a desthiobiotin modified therapeutic and a streptavidin modified hydrogel. Streptavidin was successfully immobilized onto the hydrogel via SPAAC with 70% efficiency across different concentrations (FIG. 2B).

Agarose is modified to contain an azide moiety to which a DBCO modified streptavidin is conjugated on the agarose polymer via SPAAC. The antibody therapeutic is modified with desthiobiotin. When introduced to the streptavidin modified agarose, the antibody is immobilized onto the polymer backbone due to the high affinity of desthiobiotin to streptavidin. Similarly, a sparingly soluble biotin derivative is introduced to the system, where the soluble fraction would irreversibly displace the drug from the polymer backbone due to biotin's higher affinity for streptavidin, releasing the drug and resulting in a drug delivery system where the rate of release is dictated once again by the binding kinetics of the desthiobiotin and biotin.

The main advantage of this drug delivery system is the use of a minimally modified drug conjugate. The antibody would be modified by a small molecule (biotin analog) instead of a protein (streptavidin) thus decreasing the chances of any steric effects which could change bioactivity. Desthiobiotinylated Avastin® (bevacizumab) was assessed for its ability to bind VEGF 165a in the HUVEC tube formation assay (FIG. 11C). Here, the desthiobiotynlated antibody displayed the same inhibition of tube formation as native Avastin® (bevacizumab), illustrating little to no loss in bioactivity. Additionally, toxicity studies were performed using the MTS assay using HUVEC, assessing the toxicity of the components of the drug delivery system as well as the complete drug delivery system (FIGS. 11 A and B). None of the components display any inherent toxicity except for the solid suspension of oleylbiotin. However, once incorporated together, minimal toxicity was seen even with the addition of the oleylbiotin. These results suggest the drug delivery does not display any inherent toxicity and would be amenable to in vivo testing.

Different embodiments of the application have been shown by the above examples. Those skilled in the art could develop alternatives to the methods mentioned above that are within the scope of the application and defined claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

REFERENCES

1 Gaudana, R., Jwala, J., Boddu, S. H. & Mitra, A. K. Recent perspectives in ocular drug delivery. *Pharmaceutical research* 26, 1197-1216 (2009).

2 Urtti, A. Challenges and obstacles of ocular pharmacokinetics and drug delivery. *Advanced drug delivery reviews* 58, 1131-1135 (2006).

3 Stewart, M. W. et al. Pharmacokinetic rationale for dosing every 2 weeks versus 4 weeks with intravitreal ranibizumab, bevacizumab, and aflibercept (vascular endothelial growth factor Trap-eye). *Retina* 32, 434-457 (2012).

4 T A, C. N. Minimizing the risk of endophthalmitis following intravitreous injections. *Retina* 24, 699-705 (2004).

5 Jager, R. D., AIELLO, L. P., Patel, S. C. & Cunningham Jr, E. T. Risks of intravitreous injection: a comprehensive review. *Retina* 24, 676-698 (2004).

6 Falavarjani, K. G. & Nguyen, Q. Adverse events and complications associated with intravitreal injection of anti-VEGF agents: a review of literature. *Eye* 27, 787-794 (2013).

7 Li, Y., Rodrigues, J. & Tomas, H. Injectable and biodegradable hydrogels: gelation, biodegradation and biomedical applications. *Chemical Society Reviews* 41, 2193-2221 (2012).

8 Xie, B. et al. An injectable thermosensitive polymeric hydrogel for sustained release of Avastin® to treat posterior segment disease. *International journal of pharmaceutics* 490, 375-383 (2015).

9 Rauck, B. et al. Biocompatible reverse thermal gel sustains the release of intravitreal bevacizumab in vivo. *Investigative ophthalmology & visual science* 55, 469-476 (2014).

10. Mitragorti, S, Burke, P A, Langer, R. (2014) Overcoming the challenges in administering biopharmaceuticals: formulation and delivery strategies. *Nat. Rev. Drug Disc.* 13, 655-672

11. Pakulska, M M, Miersch, S, Shoichet M S. (2016) Designer protein delivery: from natural to engineered affinity-controlled release systems. *Science* 351, 1279.
12. Freeman, I, Kedem, A, Cohen, S. (2008) The effect of sulfation of alginate hydrogels on the specific binding and controlled release of heparin-binding proteins. *Biomaterials* 29, 3260-3268
13. Vulic, K, Shoichet M S. (2012) Tunable growth factor delivery from injectable hydrogels for tissue engineering. *J. Am. Chem. Soc.* 134, 882-885
14. Zhou, Z, Xiang, Y, Tong, A, Lu, Y. (2014) Simple and efficient method to purify DNA-protein conjugates and its sensing applications. *Anal. Chem.* 86, 3869-3875
15. Garcia-Aljaro, C, Munoz, F X, Baldrich, E. (2009) Captavidin: a new regenerable biocomponent for biosensing? *Analyst* 134, 2338-2343
16. Chivers, C E, Crozat, E, Chu, C, May, V T, Sherratt, D J, Howarth, M. (2010) A streptavidin variant with slower biotin dissociation and increased mechanostability. *Nat. Meth.* 7, 391-393
17. Woodley, D W, Longsworth, L G. (1942) Isolation of an antiobiotin factor from egg white. *J. Biol. Chem.* 142, 285-290
18. Kawato, T, Mizohata, E, Shimizu, Y, Mechizuka, T, Yamamoto, T, Takasu, N, Matsuoka, M, Matsumura, H, Kodama, T, Kanai, M, Doi, H, Inoue, T, Sugiyama, A. (2015) Structure-based design and synthesis of a bivalent iminobiotin analog showing strong affinity toward a low immunogenic streptavidin mutant. *Biosci. Biotech. Biochem.* 79, 640-642

What is claimed is:

1. A drug release formulation comprising:
   a) a drug conjugate comprising a drug bound to a first member of an affinity binding pair;
   b) a second member of the affinity binding pair, wherein the drug conjugate reversibly binds to the second member of the affinity binding pair to form a complex; and
   c) a competitive binding compound that disrupts the binding between the drug conjugate and the second member of the affinity binding pair to result in drug release,
   wherein at least one of the first and second members of the affinity binding pair are bound to or encapsulated in a supporting matrix, and
   the competitive binding compound is comprised in the supporting matrix in a form selected from insoluble pellets and insoluble particles, and
   wherein the first member of the affinity binding pair is a protein with a binding affinity for biotin selected from streptavidin and a streptavidin derivative, the second member of the affinity binding pair is selected from desthiobiotin and a desthiobiotin derivative, and the competitive binding compound is selected from biotin and a biotin derivative, or
   the first member of the affinity binding pair is selected from desthiobiotin and a desthiobiotin derivative, the second member of the affinity binding pair is a protein with a binding affinity for biotin selected from streptavidin and a streptavidin derivative, and the competitive binding compound is selected from biotin and a biotin derivative.

2. The formulation of claim 1, wherein the supporting matrix is selected from one or more of a hydrogel, nanoparticle and microparticle.

3. The formulation of claim 2 wherein the supporting matrix comprises agarose.

4. The formulation of claim 1, wherein the protein with a binding affinity for biotin is selected from streptavidin and a streptavidin derivative.

5. The formulation of claim 1, wherein the protein with a binding affinity for biotin is streptavidin.

6. The formulation of claim 1, wherein the protein with a binding affinity for biotin is a streptavidin derivative selected from captavidin, traptavidin and neutravidin.

7. The formulation of claim 6, wherein the streptavidin derivative is neutravidin.

8. The formulation of claim 1, wherein the desthiobiotin derivative is iminobiotin.

9. The formulation of claim 1, wherein the competitive binding compound is selected from biotin and a hydrophobic biotin derivative.

10. The formulation of claim 1, wherein the competitive binding compound is a hydrophobic biotin derivative that is a long chain biotin derivative of the formula:

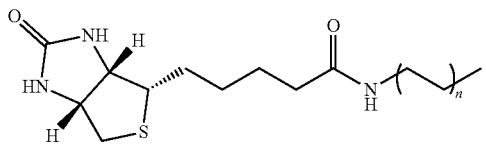

wherein, n is an integer between 1 and 20.

11. The formulation of claim 1, wherein the competitive binding compound is a hydrophobic biotin derivative selected from tert-butyl biotin, oleyl-biotin or hexadecyl-biotin.

12. The formulation of claim 1, wherein the drug is a macromolecule selected from a protein, peptide, antibody and nucleic acid.

13. The formulation of claim 1, wherein the competitive binding compound has a solubility in the supporting matrix that controls interaction of the competitive binding compound with the complex and the interaction of the competitive binding compound with the complex controls the release of the drug.

14. The formulation of claim 1, formulated for administration by injection or implantation.

15. A kit for drug release comprising
   a) a drug conjugate comprising a drug bound to a first member of an affinity binding pair;
   b) a second member of the affinity binding pair, wherein the drug conjugate reversibly binds to the second member of the affinity binding pair to form a complex; and
   c) a competitive binding compound that disrupts the binding between the drug conjugate and the second member of the affinity binding pair to result in drug release,
   wherein at least one of the first and second members of the affinity binding pair are bound to or encapsulated in a supporting matrix, and
   the competitive binding compound is comprised in the supporting matrix in a form selected from insoluble pellets and insoluble particles, and
   wherein the first member of the affinity binding pair is a protein with a binding affinity for biotin selected from streptavidin and a streptavidin derivative, the second member of the affinity binding pair is selected from desthiobiotin and a desthiobiotin derivative, and the competitive binding compound is selected from biotin and a biotin derivative, or the first member of the affinity binding pair is selected from desthiobiotin and a desthiobiotin derivative, the second member of the affinity binding pair is a protein with a binding affinity for biotin selected from streptavidin and a streptavidin derivative, and the competitive binding compound is selected from biotin and a biotin derivative.

16. A method of releasing a drug in a subject in need thereof comprising administering an effective amount of a formulation of claim 1 to the subject.

17. The method of claim 16, wherein the release of the drug is sustained over a desired period of time.

18. The method of claim 17, wherein the drug is for treatment of the eye or for treatment of a cancer.

\* \* \* \* \*